United States Patent [19]

Tarnowski

[11] 4,432,895

[45] Feb. 21, 1984

[54] MONOMERIC INTERFERONS

[75] Inventor: Stanley J. Tarnowski, Nutley, N.J.

[73] Assignee: Hoffmann-La Roche, Nutley, N.J.

[21] Appl. No.: 444,113

[22] Filed: Nov. 24, 1982

[51] Int. Cl.³ .................... A61K 45/02; C07G 7/00
[52] U.S. Cl. .................... 260/112 R; 424/85; 435/68
[58] Field of Search .............. 260/112 R; 424/85; 435/68

[56] References Cited

U.S. PATENT DOCUMENTS

| | | | |
|---|---|---|---|
| 3,548,053 | 12/1970 | Joshi | 424/85 |
| 4,061,538 | 12/1977 | Dorner et al. | 424/85 X |
| 4,184,917 | 1/1980 | Dorner et al. | 435/68 |
| 4,278,661 | 7/1981 | Knight, Jr. | 260/112 R X |
| 4,289,689 | 9/1981 | Friesen et al. | 260/112 R |
| 4,289,690 | 9/1981 | Pestka et al. | 260/112 R |
| 4,382,027 | 5/1983 | Braude | 260/112 R |

*Primary Examiner*—Howard E. Schain
*Attorney, Agent, or Firm*—Jon S. Saxe; George M. Gould; Steve T. Zelson

[57] ABSTRACT

A method for producing monomeric interferons from oligomeric interferons, for preventing formation of oligomeric interferon from monomeric interferon, and for increasing the yield of monomeric interferon upon purification of interferon is described. The method employs a redox reagent to treat the interferon sample.

11 Claims, No Drawings

MONOMERIC INTERFERONS

BACKGROUND OF THE INVENTION

Interferons are proteins which are produced by a number of different kinds of organisms and which are presently grouped into three major classes designated leukocyte interferon (IFN-α), fibroblast interferon (IFN-β) and immune interferon (IFN-γ). These interferons have antiviral and antiproliferative activites, a potent ability to confer a virus-resistant state in targeted cells and immunomodulatory activities. These biological properties have led to the clinical use of interferons as therapeutic agents for the treatment of viral infections and malignancies, which in turn has prompted a demand for a greater supply.

Interferons have been produced from natural sources such as buffy coat leukocytes and fibroblast cells, optionally using known inducing agents to increase the production of interferon. Interferons have also been produced by recombinant DNA techniques, i.e. by expression from a microorganism which has been transformed with an expression vector containing an interferon gene under the control of a promoter-operator sequence. (Leukocyte, fibroblast and immune interferons produced by recombinant techniques are designated rIFN-α, rIFN-β and rIFN-γ respectively.)

Regardless of the method of production employed, the resulting interferon must be purified, preferably to homogeneity, before it may be employed as a therapeutic agent. Interferons may be purified to homogeneity using methods described in U.S. Pat. Nos. 4,289,689 and 4,289,690 or by monoclonal antibody affinity chromatography. Presently available purification methods are carried out under conditions which can favor the formation of dimers, trimers and higher oligomers of the interferon. These oligomeric forms of interferon result from two or more interferon molecules becoming irreversibly associated with one another through intermolecular covalent bonding, such as by disulphide linkages. This problem has been observed particularly will respect to leukocyte and fibroblast interferons.

The oligomeric form in many cases has either no biological activity or lower activity than the monomeric form, or it has the potential for causing deleterious side effects if used therapeutically. It is important, therefore, to have available a method for obtaining interferons in monomeric form.

A method for obtaining fibroblast interferon in monomeric form is described in U.S. Pat. No. 4,278,661. Serum-free human fibroblast interferon is purified by adsorption on immobilized Cibacron Blue and elution of the adsorbed interferon with an aqueous buffer solution containing ethylene glycol, to provide a mixture of interferon in monomeric and dimeric form. The dimeric form is converted to monomeric form by heating the mixture in the presence of an organic thiol compound such as thioglycolic acid, 2-mecaptoethanol or dithiothreitol. The use of elevated temperatures, however, is generally not desirable in protein preparation because of a resulting diminution or complete loss of biological activity for the heated protein.

SUMMARY OF THE INVENTION

The invention relates to methods for producing biologically active monomeric interferon from a purified or partially purified sample containing oligomeric interferon; for preventing the formation of oligomeric interferon in a sample of purified or partially purified interferon; and for increasing the yield of biologically active monomeric interferon from the purification procedure. The methods involve treating the sample with an effective amount of a redox reagent having a reducing agent and an oxidizing agent capable of converting the oligomeric interferon to biologically active monomeric interferon or of maintaining biologically active monomeric interferon in a biologically active monomeric form.

Treatment of interferon with the redox reagent can provide monomeric interferon and little, if any, oligomeric interferon, increasing the yield of monomeric interferon significantly during purification of the interferon, and can eliminate the necessity of an additional purification step for separating monomeric interferon from oligomeric interferon. The treatment described herein does not require the use of elevated temperatures with concomitant reduction or loss of biological activity.

DETAILED DESCRIPTION OF THE INVENTION

Any interferons capable of forming oligomers, e.g. leukocyte and fibroblast interferons, may be treated by the methods of this invention. A preferred interferon for use herein is human leukocyte interferon.

Interferons useful in the practice of this invention can be obtained or derived from any convenient cellular sources. Cells producing interferon can be cultured and harvested, and crude extracts containing the interferon extracted therefrom by conventional methods and procedures well known in the art. One especially suitable source of interferon to which this invention relates is transformed *E. coli* cells, These *E. coli* cells may be transformed by known techniques of DNA recombination such as, for example, by the method of Goeddel et al., Nature 287, 411 (1980). Although the invention is particularly described with reference to interferon produced by *E. coli* transformants, interferons produced by other transformant microorganims may also be used.

The recombinant *E. coli* organisms (cells) can be fermented, harvested and the interferon extracted from the cells by conventional procedures such as, for example, in analogy to the procedures described by Goeddel et al., Nature 287, 411 (1980); Wetzel et al., Journal of Interferon Research I, 381 (1981) and Gray et al., Nature 295, 503 (1982). The resulting cell-free extract containing the interferon can then be processed in the manner described hereafter.

It is preferred that the interferon in the cell-free extract be purified or partially purified before treatment with the redox reagent of this invention. The minimum extent of the partial purification preferred for a cell extract containing interferon before treatment with the redox reagent is one which provides an extract essentially free of cell debris and nucleic acids. This can be accomplished using known procedures, singly or in combination, such as flocculation, salt or pH precipitation, dialysis, differential centrifugation, filtration, chromatography, and the like, with the desired protein being collected in the most active fractions.

A preferred procedure for partially purifying the cell-free extract for use in the practice of this invention is as follows:

(a) flocculation of nucleic acid and cell debris, followed by recovery of the supernatant containing the interferon after centrifugation, (b) salt precipitation of the supernatant by ammonium sulfate at approximately 65% saturation, with recovery of the precipitate containing the interferon, which may be suspended in a suitable buffer, and (c) dialysis of the suspended precipitate against the same buffer.

The above procedure can be performed by conventional methods known per se in the art. A suitable buffer in which the interferon may be suspended and dialyzed against includes any buffer which does not interfere with the biological activity of the monomeric interferon. Such buffers include any conventional buffers between pH 2.0 and 9.0, as for example singly: 0.1 M acetic acid, 0.025 M ammonium acetate, 0.1 M Tris-HCl or 0.1 M KCl/HCl. The resulting dialyzed material is suitable for further purification or for treatment with the redox reagent.

As previously indicated, the present invention provides a method for producing biologically active interferon in which essentially all of the interferon is in monomeric form which comprises treating a sample of purified or partially purified interferon with an effective amount of a redox reagent to convert oligomeric interferon to biologically active monomeric interferon and to prevent the formation of oligomeric interferon from monomeric interferon.

In a preferred embodiment of the invention, the partially purified sample (i.e. the sample with cell debris and nucleic acids removed) is first treated with the redox reagent to convert any oligomeric interferon which may be present into monomeric interferon and to prevent the formation of oligomeric interferon during subsequent purification steps. The sample may then be further purified using known techniques such as column chromatography to obtain biologically active interferon in monomeric form having the desired degree of purity. In this manner, biolgically active interferon, purified to homonogeneity, may be obtained for therapeutic use. When the partially purified sample is treated with the redox reagent prior to the final purification, the interferon in the sample is maintained in monomeric form through the final purification step so that the purified interferon obtained contains essentially only monomeric interferon.

The final purification of the treated sample in the preferred embodiment can be performed using one or more of the known chromatographic techniques such as, for example, permeation or filtration chromatography, ion-exchange chromatography, adsorption chromatography, reverse phase chromatography, high performance liquid chromatography, affinity chromatography and the like.

A preferred method for purifying the interferon-containing sample which has been treated with the redox reagent involves the use of an antibody affinity column in which monoclonal antibodies to the interferon being purified (e.g. leukocyte interferon) are bound to a solid support such as agarose. Such antibody affinity columns are known in the art, as are the conditions of operation. The interferon-containing sample is passed through the column, whereupon the interferon is selectivity bound by the monoclonal antibodies and retained in the column. Unadsorbed impurities are then washed from the column and the interferon is eluted in homogeneous form using appropriate elution solvents. The specific conditions of operation such as column size, flow rates, buffers and elution solvents employed are known in the art and are not critical to the practice of the present invention.

Alternatively to the preferred embodiment, the partially purified sample may be further purified using chromatographic techniques prior to treating the sample with the redox reagent. If one employs a chromatography column which separates proteins by molecular size, e.g. gel filtration, the monomeric and oligomeric interferons in the sample will be separated by the column and obtained therefrom as separate fractions. These fractions may be pooled and, if desired, further purified prior to treatment with the redox reagent; or the oligomer fraction may be treated with the redox reagent to convert the oligomer to monomer and then pooled with the monomer fraction, if desired, for further purification.

If the sample is purified prior to treatment with the redox reagent using chromatography columns which do not separate proteins by molecular size, e.g. antibody affinity columns, then the monomeric and oligomeric interferons will be carried through the purification process together. Thus, one can purify a sample containing both monomeric and oligomeric interferons to homogeneity prior to treating the sample with the redox reagent. This can be accomplished by purifying the sample on an affinity chromatography column employing monoclonal antibodies to the interferon being purified to produce homogeneous interferon containing both monomeric and oligomeic forms, and then treating the homogeneous interferon with the redox reagent to convert the oligomeric interferon into monomeric form. If desired, the redox reagent can be removed from the purified interferon prior to its therapeutic use by known chromatographic procedures or by dialysis against any buffer which does not interfere with the biological activity of the monomeric interferon. Such buffers preferably include any conventional buffers between pH 5.0 and 9.0. Suitable buffers include phosphate such as K-phosphate or Na-phosphate, ammonium acetate, sodium acetate, TRIS-HCl or TRICINE.

The redox reagent employed in this invention is an oxidation-reduction reagent containing a reducing agent and an oxidizing agent. The reducing and oxidizing agents are preferably in a buffer solution at pH of about 7.0–8.0, preferably pH 7.5. The buffer may be any of the aforesaid buffers capable of such pH. The reducing and oxidizing agents may be selected from any art recognized system of reducing and oxidizing agents. Among these systems there are preferred those reducing agents and oxidizing agents in combination selected from the group consisting of cysteine and cystine, cysteamine and cystamine, or selected from the group consisting of reduced and oxidized glutathione, coenzyme A, pantetheine or, provided that oxygen is present, selected from the group consisting of dithiothreitol, dithioerythreitol, 2-mercaptoethanol, 2,3-dimercaptoethanol and thioglycolic acid. The ratio of reducing agent to oxidizing agent is not critical. It is preferred that the molar ratio of oxidizing agent to reducing agent be in a range of about from 1:1000 to 1:1, most preferred is 1:10.

Treatment of the sample with the redox reagent can be carried out by simply adding the redox reagent to the sample. Temperature and pressure are not critical and can vary over a wide range from room temperature or from atmospheric pressure. It is preferred that the reaction be carried out for 12 to 24 hours at about 20° to 37° C. at atmospheric pressure.

The amount of redox reagent, i.e. reducing agent and oxidizing agent, necessary to treat a purified or partially purified sample containing interferon or oligomeric interferon is any effective amount capable of converting any oligomeric interferon in the sample to biologically active monomeric interferon and preventing the formation of oligomeric interferon from monomeric interferon. An effective amount can be from 0.0003 moles to 0.006 moles redox reagent per 0.1 to 10 grams of protein. The preferred active amount is 0.003 moles of redox reagent per gram of protein.

Interferons have exhibited antiviral, antitumor, growth inhibition and immunosuppression activity. These activities have been obtained at the clinical level using dosages $1-10 \times 10^6$ units daily using relatively crude preparations, less than 1% of which was interferon. The interferons to which the present invention relates can be formulated according to known methods to prepare pharmaceutically useful compositions, whereby the polypeptide hereof is combined in admixture with a pharmaceutically acceptable carrier vehicle. Suitable vehicles and their formulation are described in Remington's *Pharmaceutical Sciences* by E. W. Martin, which is hereby incorporated by reference. Such compositions will contain an effective amount of the interferon protein hereof together with a suitable amount of vehicle in order to prepare pharmaceutically acceptable compositions suitable for effective administration to the host.

The leukocyte interferons hereof may be parenterally administered to subjects requiring antitumor, or antiviral treatment, and to those exhibiting immunosuppressive conditions. Dosage and dose rate may parallel that currently in use in clinical investigations of human derived materials, e.g., about $(1-10) \times 10^6$ units daily, and in the case of materials of purity greater than 1 percent, likely up to, e.g., $50 \times 10^6$ units daily.

Ascending dosage tests with IFN-$\alpha$-have demonstrated that single doses as high as 198 million units can be tolerated. Generally therapeutic daily dosages in the range of from 10-100 million units can be employed, most preferably, about 50 million units. It is also possible to utilize more than one type of human interferon in concurrent therapy. Suitable dosage regimens to utilize, for example, immune interferon in conjunction with a leukocyte interferon will suggest themselves to one skilled in the art. Use of such concurrent therapy results in a synergistic enhancement of activity of the interferons and reduces the amount needed to achieve the desired therapeutic effect.

The various aspects of this invention are further illustrated by reference to the following Examples which are not meant to restrict the scope or spirit of the invention. Unless otherwise indicated in the Examples the following assays were employed or are employable in the Examples: The protein concentrations of crude extracts were estimated by the method of Bradford, *Anal. Biochem.*, 72, 248-254 (1976). The protein concentration of the material eluted from the monoclonal antibody column was estimated by use of a fluorescamine bypass apparatus coupled to a gel filtration column to eliminate the effect of Tris in the samples as described by Stein et al, *Methods Enzymol.* 79-, 7-16 (1981). Sodium dodecyl sulfate-polyacrylamide gel electrophoresis was performed as described by Laemmli, *Nature* (London), 227, 680-685 (1970). Gels were stained with silver by the method of Oakley et al., *Anal. Biochem.*, 105, 361-363 (1980).

Antiviral assays as described in Rubinstein et al., *J. Virol.*, 37, 755-758 (1981), and Familletti et al., *Methods Enzymol.*, 78, 387-394 (1981) were performed on the interferons. Cells used in the assay were bovine kidney cells (MDBK). Interferon titers were determined relative to the human leukocyte interferon reference standard obtained from the Antiviral Substances Program of the National Institute of Allergy and Infectious Diseases, Bethesda, Md.

EXAMPLE 1

Production of Oligomeric and Monomeric Interferon in Absence of Redox Reagent

This example contains the modifications of the procedures in Staehlin et al., *J. Biol. Chem.* 256, 9750-9754 (1981) and Staehlin et al., *Methods Enzymol.*, 78, 505-512 (1981) for the large scale purification of monomeric leukocyte A interferon from *E. coli* cells.

Frozen acid-killed recombinant *E. coli* cells producing human leukocyte interferon ($\pi$IFN-$\alpha$-A) were obtained as cell paste in plastic bags from a fermentation pilot plant. At the time of extraction, the storage period of the cells (in a $-20°$ C. freezer) varied from 32 days to 125 days.

The frozen paste was broken with a hammer, then passed through a meat grinder. The resulting ground slush was dropped directly into cold (4° C.) cell extraction buffer (see Table I) (4 liters per kg of cell) followed immediately with a 0.1 M solution (5 ml per 4 liters of buffer used) of phenyl methyl sulfonyl fluoride in 2-propanol. The resulting slurry was kept cold by the melting particles, was moved into the 0° C. cold room, stirred, and the pH adjusted upwards to 7.0 by gradual addition of 4 M or 6 M sodium hydroxide. Approximately 200 ml to 300 ml of 4 M sodium hydroxide was required per kg of cell paste. Two hours after the completed addition of cells to the buffer, the resulting proteinacious extraction mixture was diluted with chilled distilled water, in an open 50-gallon jacketed tank (refrigerant set at 0° C.) to a volume of 25 times the original weight of cell paste. To the stirring diluted extraction mixture was added Johns-Manville Hyflo filter-aid (about 1 kg per kg cell initially with up to another 1 kg per kg cell added as needed during filtration to maintain sufficient rate of filtration). The resulting proteinaceous slurry was filtered on a Komline-Sanderson rotary drum vacuum minifilter, which was precoated with Johns Manville Standard Super Cel. The resulting relatively dry solid shavings were discarded. 2-Octanol (about 50 ml per 10 kg batch) was used as defoamer during filtration. Although the filter itself was at ambient temperature, the temperature of the solution being handled did not rise significantly above 4° C. The filtrate was pumped from the vacuum receiver through a 0.3 u filter cartridge and a stainless steel coil immersed in ice. A conventional automated dialysis with 50 ft² membrane rated at 10,000 mw cut-off was used to concentrate the proteinacious filtrate three-fold at 4° C. The proteinacious concentrate containing interferon was filtered through a 1.2 micron filter (just prior to loading on the antibody (Ab) column) to provide a crude cell-free extract in a filtered proteinaceous concentrate containing interferon as a sample for the antibody (Ab) column.

A 10/45 cm glass column was packed with 720 ml of agarose gel to which was bound 9.2 g of monoclonal anti-interferon Li-8 antibody (in order to provide the Ab column). The operation of the Ab column (equilibration, loading, washing and elution) was automated by conventional procedure and operated using the following volumes of solutions sequentially after loading the interferon containing sample:

| Load Solution | Ab Column Bed Volumes (720 ml each) |
|---|---|
| Crude cell-free extract | 7–14* |
| Ab # 1+ | 5 |
| Ab # 2 | 5 |
| Ab # 3 | 5 |
| Ab # 4 | 5 |
| Ab # 5 (elution) | 1.5 |
| AB # 1 | 2.5 |

*Variable with content of rIFN-α-A. Based on the interferon assay, there was a loading of about 900 mg rIFN-α-A per cycle.
+Composition of each solution Ab # 1 through Ab # 5 is shown in Table 1.

The acid eluent fraction obtained by elution with Ab #5 from each cycle was combined to provide an Ab pool. The Ab tool (10 to 20 liters, typically pH 3.7 and conductivity 5.6 milliohms/0.66 cm cell) was concentrated between 0.5 liter to 1 liter at a rate of about 150 ml/min using a conventional automated dialysis with 5 ft$^2$, 10,000 mw cutoff membrane. The concentrate was diluted with 6 to 9 liters of CM #1 buffer (see Table 1). The diluted pool was again concentrated to 300–500 ml (termed retentate or CM load) using conventional procedures and transferred to a separate container. CM #1 buffer was added to the retentate as a rinse until the total volume was about 1 liter to provide a CM load solution for a CM-52 cellulose column. Typical final pH=4,4 and conductivity=2.2 milliohms/0.66 cm cell.

A 5/30 cm glass column was packed with 100 ml to 150 ml of swollen CM-52 cellulose. The cellulose was cleaned by slurrying and filtering with 0.5 N sodium hydroxide, distilled water to neutrality, 0.5 N hydrochloric acid (two times) and distilled water in that order, just prior to use. The same column once packed was used repeatedly up to three times without observable deterioration. The procedure was as follows:

The column was equilibrated (to pH 4.5) with greater than 5 bed-volumes of CM #1 buffer. The CM load solution typically contained 3 to 10 g of protein. Using a peristaltic pump, a flow rate of 20 ml/min or a pressure of 15 psi was reached and maintained, whichever came first. Column effluent was monitored with a conventional flow cell, uv monitor and strip-chart recorder. Following loading of the CM-52 cellulose column with the CM load solution, the column was washed with CM #1 buffer until effluent was uv transparent. Elution with CM #2 buffer (see Table 1) provided one main peak (CM pool) collected manually by an operator watching the recorder. A slight amount of protein was deliberately excluded from the front and the tail of the main peak.

An amount of 7500 ml of swollen G-50 Superfine gel was packed in a 10/100 cm glass column using the following procedure:

Dry G-50 Superfine gel with a swelling volume of 0 to 11 ml/g of dry gel, was boiled with pyrogen free distilled water for 1 hour. The slurry was cooled at 4° C. overnight and poured into a 10/100 cm glass column with a packing reservoir. When the gel settled the reservoir was replaced by an adapter. The column was equilibrated at a flow rate of 4 ml/min with CM #2 buffer.

CM pool (2092 ml, 2.78 mg/ml) was concentrated by conventional automated dialysis procedure with 10,000 mw cutoff, and 5 ft$^2$ area using a Masterflex peristaltic pump in a 4° C. cold room. The concentrate measured 977 ml and 5.95 mg/ml. The concentrate was filtered through a 0.45 u filter just prior to loading. The above prepared column was loaded with the CM pool from the column, which CM pool was a protein solution of concentration 25 mg protein/ml and a volume not exceeding 188 ml (2.5% of total gel volume of 7500 ml). A typical batch is shown here. Five cycles were executed.

Operation of the Column

Flow rate 4 ml/min or less
Flow direction—bottom to top
Single buffer used—CM No. 2-defined in Table 1
The time cycles and volumes of elution are approximately as follows:

| | Volume | Time Required at 4 ml/min |
|---|---|---|
| Load | 187 ml | 47 min |
| Void Volume | 1867 ml | 7 hrs 47 min |
| Oligomers Peak | 680 ml | 2 hrs 50 min |
| Monomer Peak | 570 ml | 2 hrs 23 min |
| Total | 3304 ml | 13 hrs 47 min |

A conventional fraction collector/uv detector/recorder system was used to collect 24 ml fractions at 6 min per fraction. The monomer fractions to be pooled began at the second or third fraction after the rise of the monomer peak in the uv tracing (this coincided with the appearance of faint yellow color in the tube by eye) and pooled with about 25 fractions following that fraction. The monomer peak from the G-50 column (ca 1.0 mg/ml) was concentrated by conventional ultra filtration to about 5 to 6 mg/ml. The concentrate was subdivided into aliquots and stored at −20° C. All the remaining protein containing fractions (uv and visible) were pooled as oligomers.

TABLE 1

Buffered/Non-buffered Solutions Used in the Processing of 10 kg of *E. coli* Cells

| Solution Name | Approximate Volume 10 kg cells | Description |
|---|---|---|
| Cell Extraction Buffer | 60 liters | 2 M Guanidine HCl, 2% Triton X-100,0.1M Tris, pH 7.5 ± 0.2 |
| Ab # 1 | 90 liters | 0.286 M GuHCl, 0.286% Triton X-100, 0.1 M Tris HCl (pH 7.5) |
| Ab # 2 | 50 liters | 0.5 M NaCl, 0.2% Triton X-100, 0.025 M Tris, pH 7.5 |
| Ab # 3 | 50 liters | 1.0 M NaSCN, 0.1% Triton X-100, 0.025 M Tris, pH 7.5 |
| Ab # 4 | 40 liters | 0.15 M NaCl, 0.1% Triton X-100, no pH adjustment |
| Ab # 5 | 25 liters | 0.20M HOAc, 0.1% Triton X-100, 0.15 M NaCl |
| CM # 1 | 12 liters | 0.025 M NH$_4$OAc, 0.024 M NaCl, pH 4.5 |
| CM # 2 | 4 liters | 0.025 M NH$_4$OAc, 0.12 M NaCl, pH 5.0 |

EXAMPLE 2

Procedure for the Conversion of Oligomers to Monomers

Oligomeric forms were obtained by the procedure as described in Example 1. The pool of oligomers so obtained was diluted to a protein concentration of 0.28 mg/ml with 0.1 M Tris-HCl, pH 7.5. Powdered reduced glutathione (GSH) and powdered oxidized glutathione (GSSG) to concentration of $1 \times 10^{-3}$ M and $1 \times 10^{-4}$ M, respectively, were added. The resulting mixture was stirred magnetically at room temperature (20°–22° C.) for 12 hours followed by an incubation at 37° C. for an additional 12 hours. After incubation the reaction mixture was dialyzed against 0.1 M acetic acid overnight at 4° C. to produce GSH/GSSG converted monomers. The sodium dodecyl sulfate-polyacrylamide gel electrophoresis on 12.5% gels under nonreducing conditions was performed according to Laemmili, *Nature* (London) 227, 680–685 (1970). Nonreducing conditions were accomplished by omitting 2-mercaptoethanol from the sample buffer. Proteins bands on the gel electrophoresis were visualized by staining for 1 hour at room temperature with 0.2% Coomassile Brillant blue R-250 in methanol/acetic acid/water (25:10:65) and destained with 5% methanol in 10% acetic acid. The results of such gel electrophoresis reveal that the monomeric compounds obtained in the absence of redox reagent and in the presence of redox reagent have identical mobilities on gel electrophoresis, indicating that the conditions produce identical monomers. The residual dimer that remains in the converted monomer can be conveniently removed by chromatography on Sephadex G-50 as described in Example 1. Table 2 shows the antiviral activity of the oligomers, monomers and converted monomers (GSH/GSSG converted monomers) when assayed on MDBK cells according to Familletti et al., *Methods Enzymology*, 78, 387–394 (1981). The protein concentrations were estimated by the method of Bradford *Anal. Biochem.*, 72, 248–254 (1976) using monomer leukocyte A interferon as a standard.

TABLE 2

| Sample | Specific Activity (MDBK units/mg protein $\times 10^{-8}$) $\bar{x} \pm$ S.D. |
|---|---|
| I Oligomers obtained by procedure in Example 1 from Sephadex G-50 chromatography | $0.7 \pm 0.14$ |
| II Monomers obtained by procedure in Example 1 from Sephadex G-50 chromatography | $2.2 \pm 0.6$ |
| III GSH/GSSG converted monomers by the procedure in Example 2 | $1.8 \pm 0.3$ |

Table 2 above shows that the Specific Activity for the monomers (item II of Table 2) obtained in the absence of redox reagent is over 3 fold higher and the GSH/GSSG converted monomers (item III of Table 2) is over 2.5 fold higher than the Specific Activity of oligomers (item I of Table 2).

EXAMPLE 3

Characterization of Converted Monomers (1) Amino Acio Analysis

Amino analyses were performed according to the methods of Stein and Brink, *Methods Enzymol.*, 79, 21–35 (1981). The general procedure and modification for the determination of particular amino acids are described below.

1. General Procedure

Samples (about 100–200 ug) are transferred to hydrolysis tubes and dried down under vacuum. Constant boiling hydrochloric acid (approximately 150 microliters), containing 0.1% (v/v) thioglycolic acid, is added and the tubes sealed under vacuum. Hydrolysis is carried out for 24 hours at 110° C. After cooling, the tubes are opened and their contents taken to dryness under vacuum. The residues are dissolved in pH 2.2 sample diluent buffer and aliquots removed for amino acid analysis using an automated fluorescamine amino acid analyzer. A detailed description of the amino acid analyzer, buffer compositions, and chromatographic conditions follow. Amino acid analysis of samples of interferon, calibration amino acid standards and reagent blanks are carried out as indicated.

2. Modification of General Procedure for Proline Analysis

For the analysis of proline, samples are prepared and hydrolyzed according to the general procedure as described above. The analysis is carried out with a fluorescamine amino acid analyzer modified so that the reagent N-chlorosuccinimide can be combined with the column eluent just prior to the emergence of proline. The addition of this reagent is terminated after the detection of the proline peak and the remainder of the amino acid analysis is carried to completion. The composition of the N-chlorosuccinimide reagent and a description of the components of its delivery system follow.

3. Modification of General Procedure for Tryptophan Analysis

For the analysis of tryptophan, samples are prepared, hydrolyzed, and analyzed according to the general procedure with the exception that the content of thioglycolic acid in the hydrolysis mixture is raised to 4.0%.

4. Modification of General Procedure for Cysteine and Cystine Analysis

For the analysis of the sum content of cysteine and cystine (as cysteic acid), performic acid oxidation of the sample is carried out prior to hydrolysis. The conditions employed are detailed below:

a. Sample preparation. The sample to be oxidized (usually containing from 100–200 micrograms of protein) is placed in a 1.5 ml plastic micro-centrifuge tube and evaporated to dryness in vacuum.

b. Performic acid reagent. To 1.9 ml of 88% to 97% formic acid is added 0.1 ml of 30% hydrogen peroxide and the solution allowed to stand in a capped $12 \times 75$ mm plastic tube for 2 hours at room temperature. The reagent is then cooled in an ice bath to 0° C. and used immediately.

c. Oxidation of sample. The dried-down sample is allowed to cool in ice bath and 150 microliters of the cold performic acid reagent added. The tube is capped and its content mixed by vortex and allowed to stand at 0° C. for 2–2 ½ hours. The reaction is terminated by the addition of 200 microliters of ultrapure water and the solution transferred to a hydrolysis tube, frozen, and evaporated to dryness in vacuum.

d. Hydrolysis of sample and amino acid analysis. The dried-down sample is hydrolyzed and analyzed according to the general procedure with the exception that the thioglycolic acid is omitted from the hydrolysis mixture. For the purpose of comparison the cysteic acid content determined is reported as cysteine.

Table 3 compares the amino acid composition recombinant leukocyte interferon A monomer purified as described in Example 1 and monomer converted from oligomers using the GSH/GSSG redox reagent described in Example 2.

(2) Molecular Weight Estimation by SDS Polyacrylamide Gel Electrophoresis

Weber and Asborn, *J. Biol. Chem.*, 244, 4406 (1969) established that a relationship between the logarithm of molecular weight and relative mobility on a sodium dodecyl sulfate polyacrylanide gel existed. Utilizing the method of Laemmli, *Nature* (London) 227, 660–685 (1970) in absence or presence of 2 -mercaptoethanol, samples of the monomer and the converted monomer were electrophoresized, as described in Example 2. The results showed that both monomers migrate with the same relative mobility and have a molecular weight estimate of approximately 19,000 daltons.

(3) Size Exclusion High Performance Liquid Chromatography

Size exclusion high performance liquid chromatography was performed on samples of purified leukocyte A monomer and converted monomer. Two columns containing Bio-Sil TSK 2000 SW gel (7.5 mm I.D.×300 mm) were connected in tandem. Ten micrograms of protein were injected and the chromatogram developed with a buffer containing 0.1 M sodium phosphate buffer, pH 6.5 and 0.2 M $Na_2SO_4$. The flow rate was 0.5 ml/min and the effluent from the column was monitored by a UV monitor at 210 nm wavelength. The HPLC pump and UV detector were from Perkin-Elmer, the injector from Watus Associates, and the computer system for data presentation was from Tektronics and Computer Inquiry Systems.

(4) Specific activity of Interferon Forms

Leukocyte A interferon purified from recombinant *E. coli* cells can be purified as described in Example 2. If the Sephadex G-50 chromatography step is replaced with a Sephadex G-75 chromatography, the oligomeric forms can be further fractionated. Table 4 shows the bioactivity of the peak areas from Sephadex G-75. Protein was determined by the method of Lowry et al., *J. Biol. Chem.*, 193, 265–275 (1951) and the biological activity was measured on MDBK cells according to Familletti et al., *Methods Enzymol.*, 78, 387–394 (1981).

TABLE 3

| | Residues/165 Amino Acids | | Redox |
|---|---|---|---|
| Amino Acid Residue | Theoretical+ | Purified Monomer | Converted Monomer |
| Aspartic Acid & Asparagine | 12 | 14.0 | 12.5 |
| Threonine | 10 | 9.8 | 9.6 |
| Serine | 14 | 11.8 | 12.5 |
| Glutamic Acid & Glutamine | 26 | 25.0 | 25.8 |
| Proline | 5 | 5.7 | 6.3 |
| Glycine | 5 | 5.6 | 5.2 |
| Alanine | 8 | 8.4 | 8.2 |
| Valine | 7 | 6.9 | 6.4 |
| Methionine | 5 | 4.2 | 4.7 |
| Isoleucine | 8 | 8.1 | 7.5 |
| Leucine | 21 | 22.7 | 21.1 |
| Tyrosine | 5 | 5.6 | 4.9 |
| Phenylalanine | 10 | 11.0 | 10.1 |
| Histidine | 3 | 3.1 | 2.9 |
| Lysine | 11 | 10.3 | 11.0 |
| Arginine | 9 | 8.5 | 9.5 |
| Cysteine | 4 | 3.7 | 4.3 |
| Tryptophan | 2 | 1.3 | 2.5 |

+R. Wetzel et al., J. Interferon Res. 1,381 (1981)

TABLE 4

| G-75 Fraction | Specific Activity × $10^{-8}$ MDBK units/mg protein |
|---|---|
| Trimer and higher oligomers | 0.34 |
| Dimer | 0.53 |
| Monomer | 2.3 |

EXAMPLE 4

Partial Purification of Interferons

Recombinant *E. coli* cells having therein a leukocyte interferon gene were grown to an optical density of 0.7 at 550 nm in 1–3 liters of culture media containing 0.4% casamino acids and 0.4% glucose. The cells were sedimented and then washed once in buffer containing 10% sucrose, 0.1 M Tris-HCl (pH 7.5), 5 mM ethylenediaminetetra acetic acid (EDTA), 0.2 M NaCl and 0.1 mM phenylnethylsulfonyl fluoride, followed by suspension in the same buffer. The cells were homogenized in an homogenizer with two passes, one at about 6000 psi, the other at about 1000 psi. To the resulting homogenate was added Polymin P (0.35% w/v) and then the homogenate was centrifuged up to 8500 RPM for 30 minutes in a Sorvall centrifuge to remove cell debris. To the supernatant thereafter obtained was slowly added ammonium sulfate to 65% saturation and the resulting precipitate collected after centrifugation, suspended in the aforementioned buffer, and dialyzed against same buffer until conductivity was less than about 2 mM as measured by Radiomer dip probe cell constant 1.0 cm. The dialysate was then centrifuged to remove insoluble particulate at about 7500 RPM for about 20 minutes in a Sorvavl centrifuge. The resulting supernatant contained interferons and was sufficiently partially purified to be treated with the redox reagent of the present invention in a manner analogous to the procedure described in Example 2.

EXAMPLE 5

Redox Reagent Added After Antibody Column

Antibody pool (Ab-pool) containing oligomeric and monomeric forms were obtained as described in Example 1. The Ab-pool so obtained was diluted to a protein concentration of 0.3 mg/ml and the pH was adjusted with Tris-base to pH 7.5 (final concentration 0.1 M). Powdered cysteine (CSH) and powdered cystine (CSSC) to a concentration of $1 \times 10^{-3}$ M and $1 \times 10^{-4}$ M, respectively, were added. The resulting mixture was stirred magnetically at room temperature for 12 hours followed by an incubation at 37° C. for an additional 12 hours. After incubation the reaction mixture was dialyzed against 0.1 M acetic acid overnight at 4° C. to produce CSH/CSSC converted monomers. The sodium dodenyl sulfate-polyacrylanide gel electrophorisis on 12.5% gels was performed as described in Example 2. Any residual dimer that remained in the converted monomer can be conveniently removed by chromatography on Sephadex G-50 as described in Example 1. In addition to removing the residual dimer the Sephadex G-50 chromatography will remove residual redox components and Triton X-100 from the Ab-pool material.

What is claimed is:

1. A method for producing biologically active interferon in which essentially all of the interferon is in monomeric form which comprises treating a sample of purified or partially purified interferon with an effective amount of a redox reagent to convert oligomeric interferon to biologically active monomeric interferon and to prevent the formation of oligomeric interferon from monomeric interferon.

2. A method according to claim 1 wherein the interferon is recombinant human leukocyte interferon.

3. A method according to claim 1 wherein the redox reagent is selected from a group consisting of reduced glutathione and oxidized glutathione, cysteine and cystine, and cysteamine and cystamine.

4. A method according to claim 1 wherein the redox reagent is a buffered solution.

5. A method according to claim 4 wherein the buffered solution is about pH 7.5.

6. A method for producing biologically active monomeric interferon in a sample containing purified or partially purified oligomeric interferon, the method comprising treating the sample with an effective amount of a redox reagent to convert the oligomeric interferon to biologically active monomeric interferon.

7. A method according to claim 6 wherein the interferon is recombinant human leukocyte interferon.

8. A method according to claim 6 wherein the redox reagent is selected from a group consisting of reduced glutathione and oxidized glutathione, cysteine and cystine, and cysteamine and cystamine.

9. A method according to claim 6 wherein the redox reagent is a buffered solution.

10. A method according to claim 9 wherein the buffered solution is about pH 7.5.

11. A method for preparing interferon in monomeric form from a sample of partially purified cell-free extracts containing interferon comprising:
(a) passing the sample through an affinity chromatographic column which contains anti-interferon antibody which binds the interferon;
(b) washing the column with a solution which will remove non-antibody binding material from the column but which will not significantly affect the antibody bound interferon;
(c) eluting the column with a solution which will provide active fractions containing the interferon; and
(d) treating the active fractions with an effective amount of a redox agent to provide thereby active fractions containing interferon in monomeric form.

* * * * *